United States Patent
Lingenhöle et al.

(12) 
(10) Patent No.: US 6,638,068 B2
(45) Date of Patent: Oct. 28, 2003

(54) MEDICAL HANDPIECE HAVING A ROD-SHAPED GRIP PART

(75) Inventors: Bernhard Lingenhöle, Warthausen (DE); Thomas Braun, Biberach (DE)

(73) Assignee: Kaltenbach & Voigt GmbH & Co., Biberach/Rib (DE)

( * ) Notice: Subject to any disclaimer, the term of this patent is extended or adjusted under 35 U.S.C. 154(b) by 0 days.

(21) Appl. No.: 09/872,605

(22) Filed: Jun. 1, 2001

(65) Prior Publication Data

US 2002/0009691 A1 Jan. 24, 2002

(30) Foreign Application Priority Data

Jun. 2, 2000 (DE) ......................................... 100 27 387
Mar. 26, 2001 (DE) ......................................... 101 14 656

(51) Int. Cl.[7] ............................................... A61C 1/10
(52) U.S. Cl. ...................................... 433/114; 433/133
(58) Field of Search ................................ 433/114, 118, 433/133, 119, 29, 124, 125, 126, 131

(56) References Cited

U.S. PATENT DOCUMENTS

| 623,469 | A | * | 4/1899 | Hailer |
|---|---|---|---|---|
| 1,039,420 | A | * | 9/1912 | MacDonald |
| 3,092,908 | A | * | 6/1963 | Flatland |
| 4,183,140 | A | | 1/1980 | Rieselman |
| 4,276,025 | A | | 6/1981 | Straihammer ............... 433/105 |
| 4,303,393 | A | * | 12/1981 | Gentry ........................ 433/130 |
| 5,052,924 | A | | 10/1991 | Berg |
| 5,251,025 | A | * | 10/1993 | Cooper et al. ................. 433/29 |
| 5,484,283 | A | * | 1/1996 | Franetzki .................... 433/116 |
| 5,575,647 | A | * | 11/1996 | Grubbs ........................ 433/114 |
| 5,908,294 | A | | 6/1999 | Schick et al. |

FOREIGN PATENT DOCUMENTS

| DE | 199 09 407 A | 9/1999 |
|---|---|---|
| DE | 198 48 556 A1 | 4/2000 |
| EP | 0 054 653 A | 6/1982 |
| WO | WO 96/41583 | 12/1996 |

OTHER PUBLICATIONS

International Search Report in German 10027387 dated Jun. 2, 2000.
English language Abstract of DE 199 09 407 A1.
English language Abstract of EP 0 054 653 A2.
2 pages from Supplemental European Search Report dated Mar. 15, 2002, and citing the above documents.

* cited by examiner

Primary Examiner—Ralph A. Lewis
(74) Attorney, Agent, or Firm—Marshall, Gerstein & Borun

(57) ABSTRACT

The invention relates to a medical, in particular dental-medical handpiece (3) having a rod-shaped grip part in the forward end region of which there is arranged a holding device (5) having a lateral insertion opening (13) for a working tool (6), whereby the middle axis (5a) of the insertion opening (13) includes, with the middle axis (3c) of the grip part extending rearwardly from the point of intersection with the middle axis (5a), an obtuse angle (W2). In order to improve the suitability of the handpiece (3) also for use in small spaces of the body to be treated, a forward grip section (3b) of the grip part is curved towards the side (14) of the handpiece (3) away from the insertion opening (13), and the obtuse angle (W2) is smaller than 103° and greater than 95°.

12 Claims, 3 Drawing Sheets

MEDICAL HANDPIECE HAVING A ROD-SHAPED GRIP PART

TECHNICAL FIELD

The invention relates to a medical handpiece having a rod-shaped grip part having a holding device disposed in a forward end region with a lateral insertion opening for a working tool defining an obtuse angle between the respective axes of the insertion opening and the gripping part of the handpiece.

DESCRIPTION OF THE RELATED ART

Such a handpiece serves for the treatment or material removing working of the human or animal body with a movable, in particular rotatable tool, and is required to fulfil inter alia two main requirements. On the one hand it should have an ergonomically favourable constructional form, so that the operating person is able to hold the handpiece with the operating hand with an effort in terms of manipulation and use of force which is as little as possible, and further is able to move the handpiece to and at the treatment site in order to carry out the treatment or the material removing working. Thereby, in many cases of working, precision working is to be carried out which requires a precise movement of the handpiece, e.g. when working up a cavity or when working on a tooth stump of a tooth for a dental crown. One condition for this is that the operating person can ergonomically favourably grip the handpiece. On the other hand, the handpiece should be of such a constructional form that it can also been used in a readily manipulable manner when the working site is located in a body aperture, such as is e.g. the case with a mouth. Here it is to be striven for that the handpiece should also be advantageously employable even with restricted space and visibility conditions.

For fulfilling the first requirement, a so-called angled handpiece has been developed which has an acutely angled neck part which at its free end is thickened in a head-like manner and has a holding device with a lateral insertion opening for a tool. Due to the lateral acute angling, the grip part has a bend, whereby the insertion opening and the tool inserted therein are located on that side of the grip part toward which the bend faces. Such an angled tool be gripped manually ergonomically favourably and can be guided when working, whereby e.g. pressure is exercised on the handpiece with a finger of the operating hand in its concave bend region. By these means, when working, the handpiece is located in a stable condition which makes possible a movement of the handpiece under the applied pressure in a readily manipulable manner. This known angled shape of the handpiece has also proved to be advantageous in the case of restricted space conditions at the site of treatment, in particular in the region of a mouth. Thereby, the angled handpiece is introduced into the body aperture through the body aperture opening in a per se known and conventional grip position of the operating hand, whereby also here the position of the angled handpiece which is stable in consideration of the pressing forces on the tool advantageously comes about of itself.

A dental medical handpiece of the kind indicated in the introduction, in the shape of an angled handpiece, is described in WO 96/41583. With this known angled handpiece the middle axis of a holding device integrated into the angled holder limb includes an obtuse angle of 130 to 107° with the middle axis of the angled holder limb. This constructional form is intended to be particularly adapted with regard to the anatomical relationships of human jaws, so that it is intended to be possible, in the restricted space available between the upper and lower jaw, to work on the teeth also in the rearward region (molars) in a favourable position.

There has furthermore become known a turbine handpiece in the form of an angled handpiece, with which the middle axis of the holding device includes an obtuse of 95° with the section of the middle axis of the angled neck part extending rearwardly from the intersection point of this middle axis.

SUMMARY OF THE INVENTION

The object of the invention is to so configure a medical or dental-medical handpiece of the kind indicated in the introduction, that its suitability for use also in small spaces is improved. In particular, its shaping is to be improved in consideration of the anatomical form of the human jaw or the human open mouth.

According to the invention, a forward grip section of the grip part is curved toward the side of the end piece away from the insertion opening at an obtuse angle greater than 95° and small than 103°.

With the configuration in accordance with the invention, a forward grip section of the grip part is curved towards the side of the handpiece away from the insertion opening, and the middle axis of the insertion opening of the holding device includes with the middle axis of the handpiece an angle which is smaller than 103° and greater than 95°, advantageously about 100°. In tests it has proved that just this angular range, taking into account an imaginary line or curve in space, in which the tooth tips of an average lower jaw of the human jaws lie, is particularly well adapted and thus favourable. By these means it is possible to reach not only the teeth in the forward region of the lower jaw but also in the rearward region in spatially favourable manner, so that the working surface on the respective tooth can be worked in a specific position of the handpiece without the handpiece coming into collision with the boundaries of the mouth or with the teeth of the lower or upper jaw, and without the lower jaw having to be opened extremely wide. By these means a significant improvement is attained, which substantially facilitates the working, because the patient can be treated with an ergonomically favourable manipulation by the operating person even in the case of a smaller mouth opening. Thereby, the operating person can give more attention to the quality of the working or treatment. The configuration in accordance with the invention thus leads to an improvement both for the patients and also for the operating person or the dentist.

The curvature is preferably adapted to the anatomical curve shape or curve of a curve or line containing the tooth tips of an average lower jaw of the human body. The curvature may be uniform or may be progressive with increasing distance from the holding device for the tool.

A further measure, to further improve the spatial situation, taking into account the restricted spatial conditions, consist in that the handpiece or its head is so configured that the side surface of the head towards the tool lies on an extension of the line of curvature.

Both above-mentioned measures contribute to the adaptation of the handpiece to the anatomical form of the lower jaw. In the first case, at least the outer side of the curved grip section follows the curve shape of a line containing the tooth tips of the lower jaw. By these means a maximum exploitable space for movement is available for the handpiece when working, which is bounded in the direction towards the lower jaw by its teeth. With this configuration in accordance with the invention the handpiece can exploit to the maximum extent the space available for movement. These advantages can be achieved not only when working lateral inner or outer surfaces, or lateral cavities, on the tooth, but also when working up occlusal cavities. Due to the spatially favourable shaping relatively long tools or working sections can also be used.

There are also medical handpieces which serve not for a material removing working of the human or animal body but for another kind of treatment, for example taking an image of the treatment site by means of light inlet arranged laterally in the forward end region of the handpiece, from which light inlet an image or light conductor extends rearwardly.

With such a handpiece the operating person does not need to carry out precision machining work with the handpiece, and needs only to exercise a holding force on the handpiece. In technical terminology such a handpiece is called a "special purpose handpiece".

The object of the invention is to improve the spatial form of such a handpiece.

According to one embodiment of the invention, a forward longitudinal region of the handpiece is curved towards the side away from the light inlet.

The handpiece in accordance with this embodiment of the invention is, in its forward region, curved towards the side away from the inlet opening. By these means the handpiece can be ergonomically favourably manipulated at most of the treatment sites which arise when treating the human or animal body, whereby the operating hand gripping the handpiece can be moved in a readily manipulable manner. This is made possible by means of the curved form of the handpiece, with which the grip region of the rearward region of the handpiece rises up from the vicinity of the treatment site and thus a larger free space is available at least for the rearward region of the handpiece and for the operating hand.

The configuration in accordance with the invention is suited in particular for a dental-medical handpiece which is set up for the purpose of making images or video images of the teeth in the mouth of the patient. Such a handpiece in accordance with the invention is favourable not only with regard to the anatomical curvature shape or curve of a curve or line containing the tooth tips of an average lower jaw, but it is suitable also for the teeth of the upper jaw and for all conceivable treatment sites in the mouth, because the spatial form in accordance with the invention is favourable with regard to the position of the teeth and the mouth opening and therefore the handpiece can be favourably positioned with its light inlet in the mouth.

Preferred embodiments of the invention include elements which further improve the spatial form and contribute to readiness of manipulation.

Other further developing features of the invention make it possible to illuminate the treatment site, to adjust the focus of the handpiece, to simplify the construction of the handpiece, and to improve the security of gripping of the handpiece and also the appearance of the handpiece.

BRIEF DESCRIPTION OF THE DRAWINGS

Below, the invention and further advantages which can be achieved thereby will be described in more detail with reference to advantageous configurations of a preferred example. There is shown.

DESCRIPTION OF THE VARIOUS EMBODIMENTS

Figure 1:
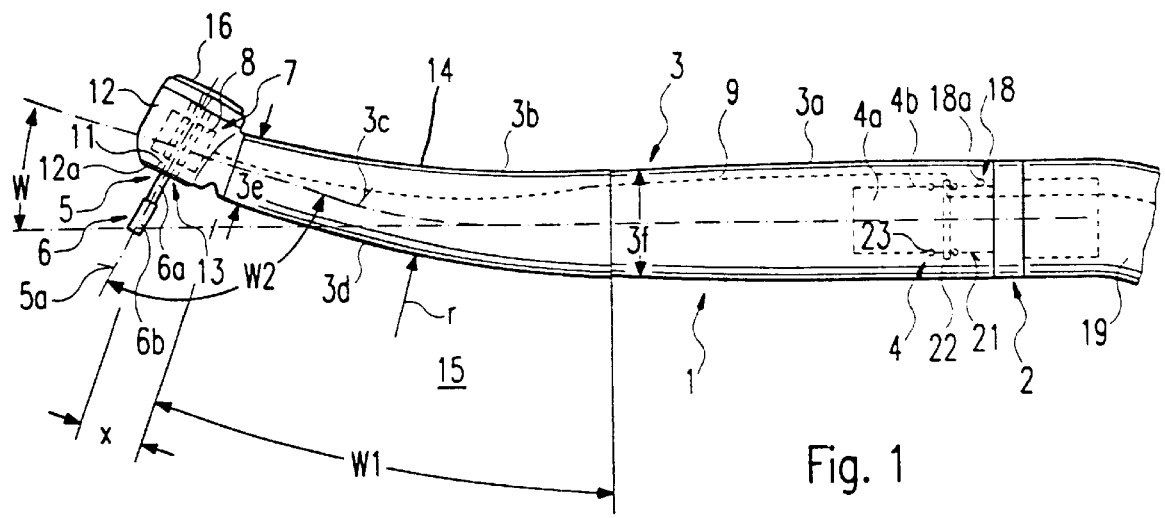
FIG. 1 a dental-medical treatment instrument in accordance with the invention, having a handpiece, in a side view.

The main parts of the treatment instrument, which is generally designated by 1, are a connection part 2 forming the rearward end of the treatment instrument 1, the handpiece 3, which is releasably connected with the connection part 2 by means of a quick coupling 4, in the form of a plug-in coupling, in particular a plug-in/turn coupling, and in the coupled condition extends forwardly in the form of a rod-shaped grip part from the connection part 2, a holding device 5, arranged in the forward end region of the handpiece 3, for a treatment or working tool 6, and a drive motor 7 which may be arranged in the region of the connection part 2 or in the region of the handpiece 3 and in the case of the present exemplary embodiment is formed by a turbine 8 integrated into the forward end region of the handpiece 3, as is known per se for so-called turbine handpieces.

If the drive motor 7 is located in the connection part 2 (not illustrated) a drive shaft is rotatably mounted in the handpiece 3 which drive shaft, in the condition in which the handpiece 3 is coupled with the connection part 2, stands in drive connection with the drive motor by means of a plug-in coupling, which by the removal of the handpiece 3 from the connection part 2 is self-actingly released. The forward end of the drive shaft is drivingly connected with a drive sleeve of the holding device 5 in which the working tool 6 can be inserted, fixed for rotation and axially positioned.

With the present exemplary embodiment, in which a turbine 8 is provided, a compressed air line 9 extends longitudinally through the treatment instrument 1 to the turbine 8 and, if applicable, also a discharge line for expended compressed air, which will be described further below. The holding device 5 is formed by means of the receiving sleeve 11 on which the turbine wheel of the turbine 8 sits and which is rotatably mounted in the preferably thickened handpiece head 12 of the handpiece 3. The receiving sleeve 11 is open at its one end, whereby an insertion opening 13 for a shaft 6a of the working tool 6 is formed, the working section of which tool, provided with a abrasive or with cutting faces, is designated 6b. The forward grip part section having the handpiece head 12 is arranged angled towards one side 14 of the handpiece 3, whereby the acute angle W in the angled region lies between 10° and 28°, preferably being about 19°. The working tool 6 is insertable into the receiving sleeve 11 from the opposite side 15 of the handpiece 3, whereby upon insertion it is self-actingly connected with the receiving sleeve 11 in a manner fixed for rotation and axially positioned therein against an unintended removal. For the purpose of releasing the working tool 6 there may be arranged an actuating element 16 on the side 14 of the handpiece head 12 opposite to the insertion opening 13, upon the manual displacement of which actuating element against the handpiece head 12 the axial positioning of the receiving sleeve 11 is released, so that the tool 6 can be drawn out axially towards the side 15.

By means of the quick-fastening coupling 4, the manipulability of the handpiece 3 is substantially improved, because the connection part 2 does not need to take part in rotating movements of the handpiece 3 during the treatment or working and therefore rotation compensation can occur. The plug-in/turn coupling has a hollow cylindrical coupling pin 4a on one coupling part and a coupling recess 4b, receiving the coupling pin 4a with slight play for movement. With the present configuration the coupling pin 4a extends from the connection part 2 forwardly and the coupling recess 4b is arranged in the rearward end region of the handpiece 3. For the releasable positioning of the plug-in coupling in the coupling position there serves a latching device 18, which can be manually overcome, having a latching element 18a mounted transversely movably, which latching element is arranged in a recess in the outer surface of the plug-in pin 4a or in the inner surface of the plug-in recess 4b and is so pressed by means of an elastic spring force into a latching recess arranged in the respectively opposing other part that the latching element 18a can spring out and the latching device 18 can be overcome by means of an axially directed and manually readily applicable pulling force.

The connection part 2 is connected, by means of a schematically illustrated flexible supply line 19 connected therewith, in particular by means of a flexible supply tube, with a non-illustrated control apparatus, as is per se known with a medical or dental-medical treatment station. The compressed air line 9 extends through the supply line 19 and through the treatment instrument 1, and there may also extend at least one further medium line, for example for light, air, water and/or spray, which so extend through the plug-in/turn coupling 4 that the passage in the medium line or lines is ensured in any rotational position. The at least one medium line 9 can pass through the joint 21 between the plug-in pin 4a and the plug-in recess 4b in an annular groove in a Z-shape, whereby the section of the medium line 19 radially penetrating through the joint 21 is sealed by means of sealing rings 23 arranged to both sides of the annular groove 22, which sealing rings are arranged in an outer annular groove of the plug-in pin 4a or in an inner annular groove of the plug-in recess 4b.

The rod-shaped grip part of the handpiece consists of a rearward grip section 3a, which preferably extends in a straight manner, and a forward grip section 3b, adjoining thereon, which develops in a manner curved towards the surface 14 away from the insertion opening 13. The curvature may be uniform, in particular in the shape of a section of a circular arc, or can be formed to be decreasing in the forward direction, i.e. the grip section 3b can be more strongly curved in its rearward region than in its forward region. The angle region W1, in which the curve develops, may be 10° to 28°, in particular 19°. The outlet radius of curvature r may be about 145 mm to 175 mm, in particular about 160 mm. The length of the curve section 3b may be about half of the overall length of the rod-shaped grip part. The middle axis 5a of the holding device 5 includes, with the section of the curved middle axis 3c extending rearwardly from the intersection point, or with a tangent of the forward grip section 3b touching the curved middle axis 3c at the point of intersection, an angle W2 which is greater than 95° and smaller than 103°. Preferably, the angle W2 is about 98° to 102°, in particular about 100°. The point of intersection between the middle axes 5a and 3c may lie at the forward end of the angle region W1 or have an axial spacing x from the angle region W1, as FIG. 1 in particular shows. In this case the angle W2 extends between the middle axis 5a and a tangent which touches the curved middle axis 3c at the end of the curvature these differences complicate the facts and moreover are slight, so that an angle W2 between the middle axis is 3c, 5a can be considered.

The handpiece head 12 is so arranged on the forward end of the grip section 3b that its side surface 12a towards the side 15 lies flush with an extension of the curved outer surface line 3d of the grip section 3b, or lies in substance on this extension. The grip section 3b tapers continuously and thereby uniformly or non-uniformly, e.g. decreasing forwardly, so its cross-sectional dimension 3e in the forward end region of the grip section 3b—seen in a side view—is about 9 mm. In the rearward region of the grip section 3b the corresponding cross-sectional dimension 3f may be in substance 15.2 mm. With a preferably circular cross-sectional shape of the grip section 3b the above mentioned dimensions 3e, 3f are in each case the associated outer diameters of the grip section 3b.

In the forward end region of the grip section 3b, for increasing its gripability, it is formed to the rough at its outer surface. For this purpose there may serve a non-illustrated microstructure 24, the depth of roughness of which is about 3 μm to 15 μm, preferably 6 μm. This rough outer surface can be directly worked into the outer surface of the rod-shaped grip part, which is preferably of metal, e.g. corrosion resistant steel, in particular nickel silver, or it may also be worked into the outer surface of a coating of the grip section 3b. The handpiece head 12 is preferably formed on the grip section 3b in one piece therewith. The grip sections 3a, 3b may be formed in one piece or in two pieces, and in the latter case they are fixedly connected with one another, e.g. screwed together.

Figure 2:
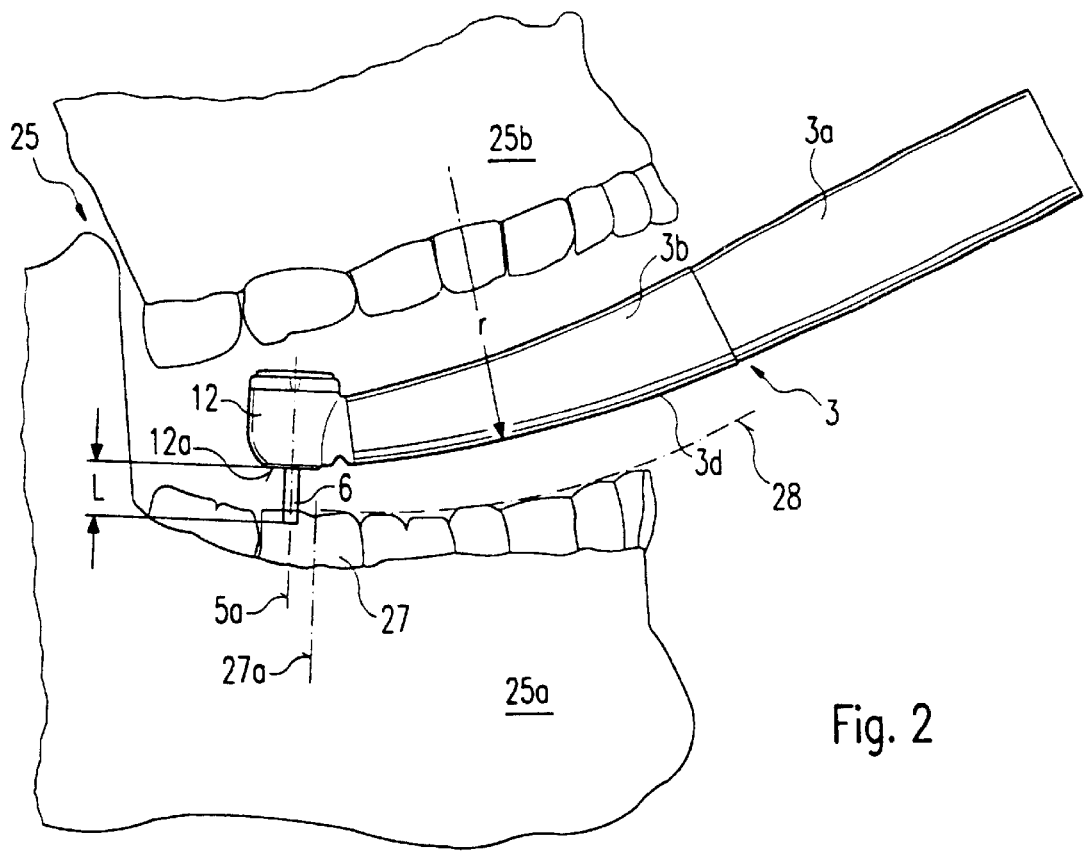
FIG. 2 the handpiece in a working position in the mouth of a human jaw, in a side view, whereby a previously known handpiece of an earlier development by the applicant/assignees is indicated in broken lines for the purpose of comparison.
Figure 3:
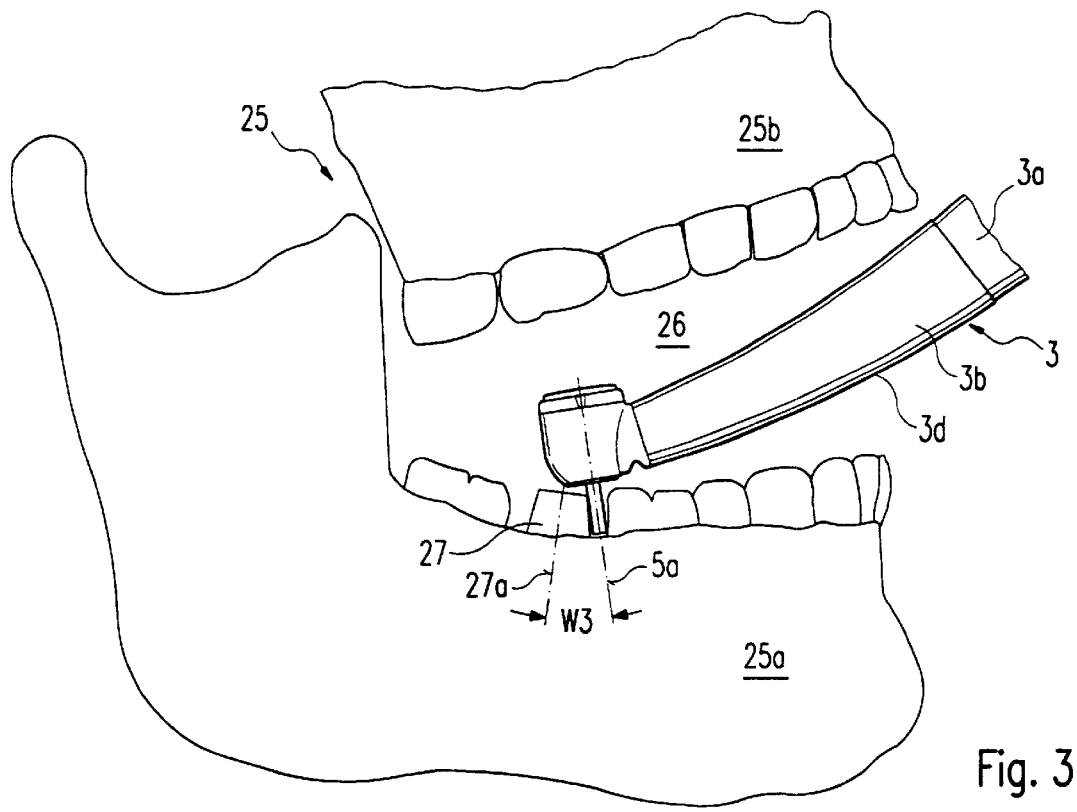
FIG. 3 the handpiece according to FIG. 2 in a different working position.
Figure 4:
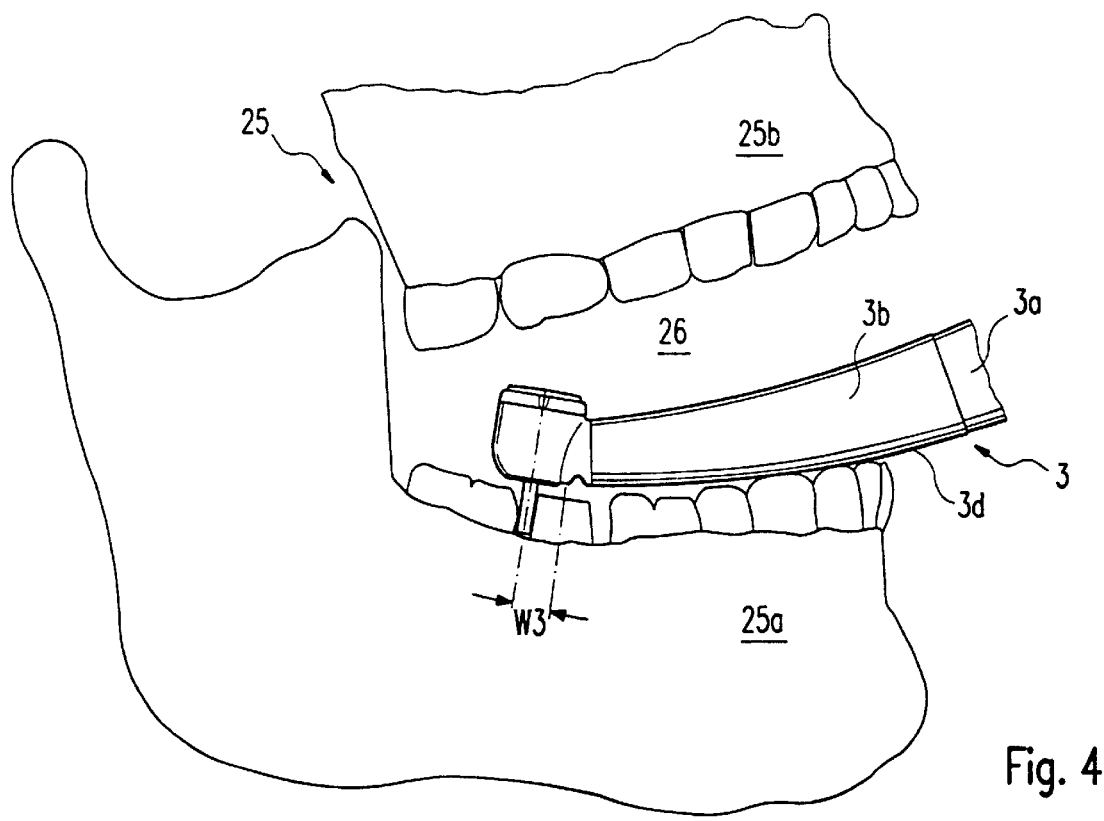
FIG. 4 the handpiece according to FIG. 2 in a further different working position.

The handpiece 3 is adapted in a particular manner to the anatomical form of an average human jaw 25, as is illustrated in FIGS. 2 to 4.

FIGS. 2 to 4 show the jaws 25 in a treatment position in which the lower jaw 25a and the upper jaw 25b are opened apart and thus the mouth 26 is opened, whereby the handpiece 3 in accordance with FIG. 2 is located in a position in which its working tool 6 is able to work up an occlusal cavity (not illustrated), whereby the tool tip is touching or is slightly penetrating into the tooth to be worked, and whereby the middle axis 5a of the working tool 6 extends approximately parallel to the middle axis 27a of the tooth 27 to be worked. FIG. 2 allows it to be recognised that the form of the handpiece 3 in particular the configuration of the grip section 3b and of the handpiece head 12 is approximately adapted to the concave lower jaw tooth curve 28 or tooth curve surface containing the tooth tips. By these means the handpiece 3 has a sufficient spacing both from the lower jaw tooth curve 28 and also from the tooth tips of the upper jaw 25b, both in its initial position of its working illustrated in FIG. 2 and also in a non-illustrated end position of its working. Thereby, the spacing to the upper jaw tooth curve 28c is slight and so great that the handpiece can be positioned at the tooth 27 to be worked without being hindered. For working, the handpiece 3 is sunk into the tooth 27. This is possible due to the sufficiently great and parallel spacing to the lower jaw tooth curve 28, since this spacing is greater than the depth of the cavity to be worked in. The length L of the working tool 6, standing up from the side surface 12a, is to dimensioned correspondingly long. The length L is e.g.

about 6 mm to 12 mm, preferably about 8 mm. From this it will be clear that with the configuration in accordance with the invention the available free space between the teeth of the jaws 25 can be advantageously exploited and a working of the teeth in a readily manipulable manner is possible. This applies in particular for the teeth in the rearward region of the mouth, namely in the region of the molars, and also for the rearmost tooth. With the configuration in accordance with the invention, between the outer side 3d of the grip part section 3b and the lower jaw tooth curve 28 there is a spacing which in substance is uniformly large, which makes possible a working depth in the tooth (depth of the cavity) corresponding to this spacing in the region of the handpiece head 12 and thereby optimally exploits this free space. This applies correspondingly also for working positions of the handpiece 3 in which, for the purposes of working up under-cuts of the cavity or conical outer surfaces e.g. for a crown, the middle axis 5a is slightly tilted with regard to the middle axis 27a of the tooth 27 to be worked. As FIG. 2 further shows the configuration in accordance with the invention also leads to a good exploitation of the free space between the handpiece 3 and the upper jaw 25b.

With the exemplary embodiment according to FIGS. 3 and 4, the handpiece 3 in accordance with the invention is employed for the preparation of the outer surface of a tooth for a dental crown. Also with this example, in which the middle axis 5a is slightly tilted with regard to the middle axis 27a of the tooth 27 to be treated, by an angle W3 of about 5°, due to the required conicity of the outer surface of the tooth, due to the configuration in accordance with the invention the free space between the handpiece 3 and the lower jaw teeth and also the upper jaw teeth can be advantageously exploited.

Figure 5:
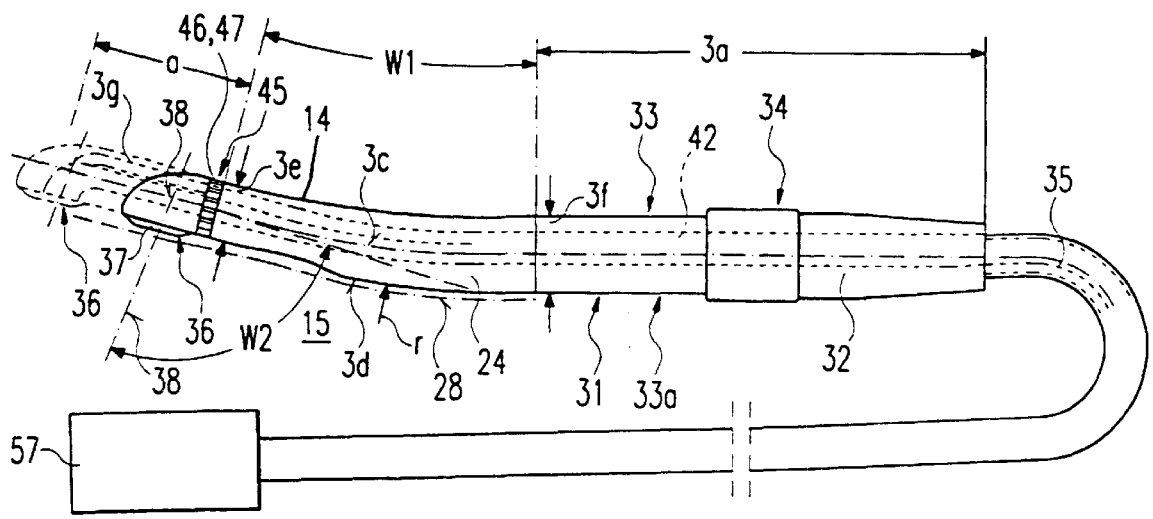
FIG. 5 a medical or dental-medical handpiece in accordance with the invention, in a modified configuration, in a side view.

The exemplary embodiment according to FIG. 5 shows a medical, in particular dental-treatment instrument 31 which can likewise consist of a connection part 32 forming the rearward end of the treatment instrument 31 and a handpiece 33 forming the remainder or forward longitudinal section of a treatment instrument 31, whereby the connection part 32 and the handpiece 33 are releasably connected with one another by means of a quick-fastening coupling 34 in the form of a plug-in coupling, which may be formed by means of a coupling pin on one coupling part and a coupling recess, formed on the other coupling part, receiving the coupling pin with slight play for movement. With this exemplary embodiment, the connecting part 32 and the handpiece 33 are so fixedly mounted on one another that although they can be parted in a workshop having appropriate tools, they cannot however be parted in a medical practice or an operating room. This applies advantageously also for the attachment of a flexible supply line 35, which is correspondingly connected with the rearward end of the connecting part 32. Since the treatment instrument 31 thus does not constitute a fixed handling unit, it is designated in the following as handpiece 33a.

The rod-shaped handpiece 33a has at its end a lateral light inlet 36, consisting of a lateral light inlet opening which is sealed by means of a protective plate 37 of light permeable material, e.g. glass or plastics, so that contaminants cannot penetrate into the light inlet 36. From the light inlet 36, a light conductor 38 extends longitudinally through the handpiece to the rear, which light conductor extends further rearwardly through the supply line 35. The middle axis 39 of the light inlet 36, extending transversely to the longitudinal middle axis 38, can include an angle of about 90° at the point of intersection with the longitudinal middle axis 38.

There is associated with the handpiece 33a in the region of the light inlet 36 an illumination device indicated overall by 41, having a light source or a light outlet which is preferably located behind the protective plate 37 so that the light source or the light outlet is also protected from contamination. The illumination device 41 may have a light conductor 42 for the delivery of light, which extends from the rear forwardly and opens in the region of the light inlet 36, preferably behind the protective plate 37, so that the light delivered through the light conductor radiates through the protective plate 37 and can illuminate the treatment site.

The elongate or rod-shaped handpiece 33a has a grip part having a rearward grip section 3a, which preferably extends in a straight manner, and continues in a forward grip section 3b adjoining thereon, which forward grip section develops curved towards the surface 14 away from the light inlet 36. The curvature may be uniform, in particular in the shape of a circular arc section, or may be decreasing in the forward direction, i.e. the grip section 3b may be more strongly curved in its rearward region than in its forward region. The angular range W1, in which the curvature develops, may be about 10° to 28°, in particular about 19°. The outer radius of curvature r may be about 145 mm to 175 mm, in particular about 160 mm. The length of the curve grip section 3b may be about half the overall length of the handpiece 33a. The middle axis 39 of the light inlet 36 encloses an angle W2, which is about 90° to 110°, with the section of the curved middle axis 3c extending rearwardly from the point of intersection or with a tangent of the forward grip section 3b touching the curved middle axis 3c at the point of intersection. Preferably the angle W2 is about 98° to 102°, in particular about 100°. The point of intersection between the middle axes 38 and 39 may lie at the forward end of the angular range W1 or have an axial spacing x from the angular range W1, as FIG. 5 shows. In this case the angle W2 extends between the middle axis 39 and a tangent which touches the curved middle axis 38 at the end of the curvature.

The light inlet 36 or the outer surface of the protection plate 37 may be flush with the outer side surface towards the side 15 or with its outer surface line 3d, or may stand out slightly from this, e.g. by a few millimeters.

The grip section 3b tapers continually and thereby uniformly or non-uniformly, e.g. decreasing forwardly, so that its cross-sectional dimension 3e in the forward end region of the grip section 3b—seen in a side view—is about 9 mm. In the rearward region of the grip section 3b the corresponding cross-sectional dimension 3f may be substantially 15.2 mm. With a preferably circular cross-sectional shape of the grip section 3b, the above mentioned dimensions 3e, 3f are in each case the associated outer diameters of the grip section 3b.

With the exemplary embodiment, the handpiece 33a extends forwardly beyond the curved grip section 3b, preferably in a straight manner. This grip section is designated with 3g and is preferably shorter than the curved grip section 3b. With such a configuration the light inlet 36 is arranged at a spacing a to the forward from the curved section 3b.

The handpiece 33a is, at least in its middle longitudinal region, here in the curved grip region 3b, formed to be rough at its outer surface, to increase its gripability. For this purpose there may serve a non-illustrated microstructure 24, the depth of roughness of which is about 3 $\mu$m to 15 $\mu$m, preferably about 6 $\mu$m. This rough outer surface can be worked directly into the outer surface of the rod-shaped grip part which is preferably of metal, e.g. corrosion resistant steel, in particular nickel silver, or can be worked into the outer surface of a coating of the grip part 3b. The handpiece head 12 is preferably formed on the grip section 3b in one piece therewith. The grip sections 3a, 3b may be formed in one piece or in two pieces, and in the later case they are fixedly connected with one another, e.g. screwed together.

The handpiece 33a has an integrated focussing device 45 which is adjustable and settable by means of an adjustment element 46 arranged on the periphery of the handpiece 33a. In the exemplary embodiment, the adjustment element 46 is formed by means of a rotatable ring 47 which is embedded into the outer surface of the handpiece 33a in a rotatable manner and is structured at its outer surface in order to improve its gripability. By means of a rotation of the adjustment ring 47 in the one or other direction of rotation, the focussing device 45 can be adjusted and set.

The handpiece 33a is adapted to the anatomical form of the average human jaw 25 in a particular manner, as is illustrated in FIG. 5, see lower jaw tooth curve 28.

Figure 6:
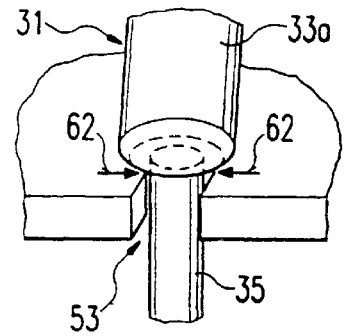
FIG. 6 a dental treatment chair in accordance with the invention, in a view from the rear.

In accordance with FIG. 6, the handpiece 33a is part of a medical or preferably dental-medical treatment chair designated overall as 51, which on one side or on both sides has a respective repository device 52 in each case having a receiving element 53 for a treatment instrument 31 or 33a preferably adjustably associated therewith. The repository device 52 may in each case be held on an adjustable carrier arm 54, 55, which projects from a carrier housing 56. Each repository device 52 may have a plurality of receiving elements 53 for further treatment instruments, e.g. at least one treatment instrument 1.

The handpiece 33a or the treatment instruments are in each case connected, by means of a plug-in connection part 57 connected with the rearward end of the supply line 35, with a counter plug-in device part 58, not shown in detail, on the repository device 52. Both plug-in connection parts 57, 58 have associated media line connections for supply media, e.g. water, air, light and electrical current, which in the plugged-together condition match to one another.

The image or light conductor 38 is connected with an imaging device (camera) in a light conducting manner, which imaging device may be integrated in a control apparatus associated with the repository device 53 or integrated into the plug-in connection part 57.

Figure 7:
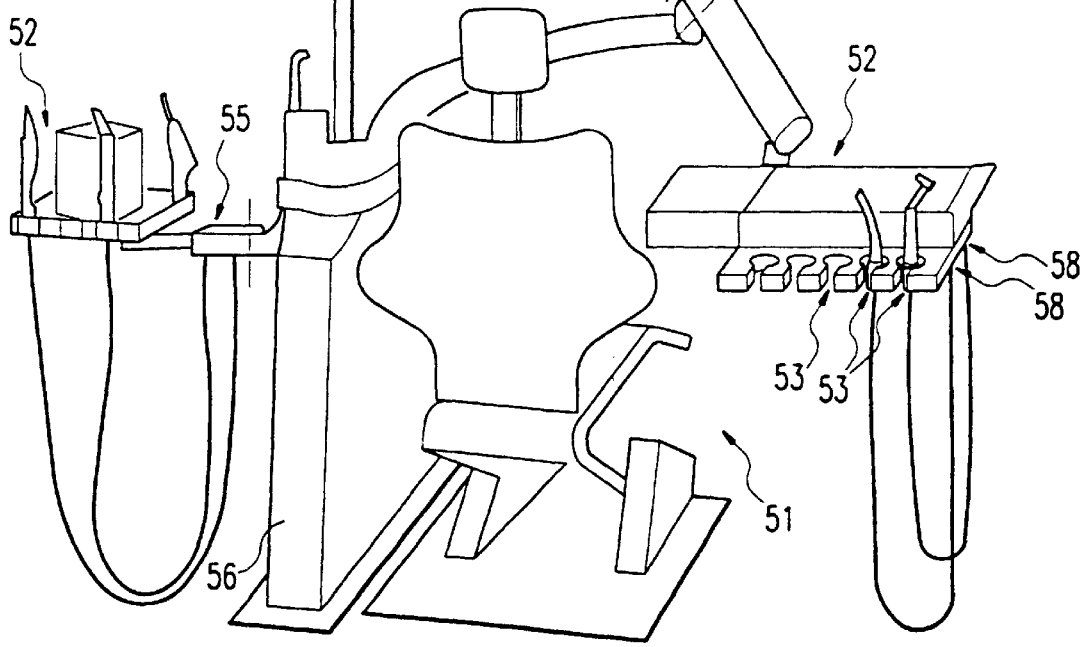
FIG. 7 a detail of a repository device for the treatment chair.

In functional operation in each case the image taken through the light inlet 36 is carried through the image or light conductor 38 to the imaging device, there converted into signals and preferably visibly displayed on a monitor 58 of the treatment chair 51. The monitor 58 is held adjustably on a carrier arm 59 which is part of a column-like carrier device 61 which is preferably supported on the housing. For switching the imaging device on and off there may be provided a switching element actuated by the operating person. For the purpose of simplifying the function it is advantageous to arrange a sensor 62 on the receiving element 63, illustrated to an enlarged scale in FIG. 7, which determines the presence and non-presence of the handpiece 33a and in each case gives a signal to the associated control device. With such a configuration, upon the removal of the handpiece 33a, the imaging device is automatically switched on and upon return switched off. The sensor 62 may be e.g. a light barrier or some other proximity switch.

There is associated with the handpiece 33a a non-illustrated protective sleeve of light permeable material, in particular plastics foil, into which the handpiece 33a can be inserted. For a treatment, the handpiece 33a is used with the protective sleeve. After its use, the protective sleeve is disinfected or sterilised, or disposed of. By these means, the handpiece 33a is protected from contamination.

What is claimed is:

1. A medical handpiece comprising:
    a rod-shaped grip part having a middle axis, a forward end region, a forward grip section and a rearward grip section;
    a holding device disposed in the forward end region and having a lateral insertion opening for a working tool in one side of the forward end region, the insertion opening having an opening axis intersecting the middle axis defining an obtuse angle between the opening axis and the middle axis in a rearward direction from the point of intersection of the said axes; and wherein
    the forward grip section of the grip part is curved at a radius of 145 mm to 175 mm toward a surface of the handpiece away from the insertion opening, defining an acute angle between the forward grip section and the rearward grip section between 10° and 28°, the obtuse angle is greater than 98° and less than 102°.

2. Handpiece according to claim 1, wherein the grip section extends over about half of the overall length of the grip part.

3. Handpiece according to claim 1, equipped with a working tool for the working of the outer contour of a tooth.

4. Handpiece according to claim 3, wherein the working tool is for the working of a dental crown.

5. Handpiece according to claim 1, equipped for speeds of rotation of the holding device for the working tool of at least 100,000 revolutions per minute.

6. Handpiece according to claim 1, comprising a turbine.

7. Handpiece according to claim 1, further comprising a handpiece head disposed on a head section of the grip part, the head section having a surface on which the insertion opening is located, said surface lying on an extension of an associated curved outer surface line of the grip section of the handpiece.

8. Handpiece according to claim 7, wherein the handpiece head is thicker in cross-section than the grip section.

9. Handpiece according to claim 1, the grip part including a longitudinal region at tapers in cross-section towards a forward end of the handpiece.

10. Handpiece according to claim 9, wherein the longitudinal region tapers continuously.

11. Handpiece according to claim 1, wherein the grip part has, in a forward region, a coating, and the microstructure is disposed on the coating.

12. Handpiece according to claim 1, wherein the microstructure has a depth of roughness of about 3 μm to about 15 μm.

* * * * *

UNITED STATES PATENT AND TRADEMARK OFFICE
CERTIFICATE OF CORRECTION

PATENT NO. : 6,638,068 B2
DATED : October 28, 2003
INVENTOR(S) : Bernhard Lingenhöle et al.

It is certified that error appears in the above-identified patent and that said Letters Patent is hereby corrected as shown below:

Column 10,
Line 47, please delete "region at tapers" and replace with -- region that tapers --.

Signed and Sealed this

Ninth Day of March, 2004

JON W. DUDAS
*Acting Director of the United States Patent and Trademark Office*